United States Patent [19]

Belgorod

[11] Patent Number: 6,060,060
[45] Date of Patent: *May 9, 2000

[54] ANALGESIC COMPOSITIONS FROM SWEET PEPPERS AND METHODS OF USE THEREOF

[75] Inventor: Barry Miles Belgorod, NYC, N.Y.

[73] Assignee: BMB Patent Holding Corporation, New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/791,567

[22] Filed: Jan. 31, 1997

[51] Int. Cl.$^7$ ............................. A61K 35/78; A23L 1/00
[52] U.S. Cl. ..................... 424/195.1; 426/425; 426/429; 426/431; 426/615; 426/655; 514/958; 514/964; 514/966; 514/967
[58] Field of Search ................................. 424/195.1, 810; 426/615, 425, 429, 431, 655; 514/964, 958, 966, 967

[56] References Cited

U.S. PATENT DOCUMENTS

| | | | |
|---|---|---|---|
| 4,313,958 | 2/1982 | LaHann | 514/627 |
| 4,400,398 | 8/1983 | Coenen et al. | 426/429 |
| 4,564,633 | 1/1986 | LaHann et al. | 514/538 |
| 4,783,465 | 11/1988 | Sunshine et al. | 514/255 |
| 4,980,190 | 12/1990 | Dunham | 426/589 |
| 5,021,450 | 6/1991 | Blumberg | 514/453 |
| 5,232,684 | 8/1993 | Blumberg et al. | 424/1.81 |
| 5,536,506 | 7/1996 | Majeed et al. | 424/464 |
| 5,660,830 | 8/1997 | Anderson | 424/195.1 |
| 5,665,360 | 9/1997 | Mann | 424/195.1 |
| 5,674,496 | 10/1997 | Eiscorn et al. | 424/195.1 |
| 5,744,161 | 4/1998 | Majeed et al. | 424/464 |
| 5,891,465 | 4/1999 | Keller et al. | 424/450 |
| 5,910,512 | 6/1999 | Conant | 514/617 |

OTHER PUBLICATIONS

Merriam–Webster's Collegiate Dictionary, Tenth Edition, Merriam–Webster, Inc., Springfield, MA, pp. 860 and 861, 1993.
The Merck Index: An Encyclopedia of Chemicals, Drugs, and Biologicals, Tenth Edition, Merck & Co., Inc., Rahway, NJ, pp. 1741 and 1742, Entry #1741, 1983.
Chemistry & Industry, No. 18, Sep. 19, 1994, p. 705.
Somos et al. Kerteszetiegyetem Kozlem., 34:5–16, English translation of abstract only, 1971.
Butkevich, Tr. Mold. Nauch.–Issled. Inst. Oroshaemogo Zemled. Ovoshchevod., 10:63–8, English translation of abstract only, 1969.
Matsushita, Eiyo To Shokuryo, 21:185–188, English translation of abstract only, 1968.
Rowland et al. (1983) "Capsaicin Production in Sweet Bell and Pungent Jalapeno Peppers" *J. Agric. Food Chem* 31:484–487.
Yuan et al. (1996) "Biostrategies in the Pacific Rim" *Genetic Engineering News* p. 29 & p. 32.
Geoffery A. Cordell et al. (1993) "Capsaicin: Identification, Nomenclature, and Pharmacotherapy" *The Annals of Pharmacotherpy* 27:330–336.
Govindarajan (1986) "Capsicum–Production, Technology, Chemistry, and Quality, Part I" *CRC Critical Reviews in Food Science and Nutrition* 22–2:109–176.
Govindarajan (1986) "Capsicum–Production, Technology, Chemistry, and Quality, Part II" *CRC Critical Reviews in Food Science and Nutrition* 23–3:207–283.
Govindarajan (1986) "Capsicum–Production, Technology, Chemistry, and Quality, Part III" *CRC Critical Reviews in Food Science and Nutrition* 24–3:245–355.
Govindarajan (1987) "Capsicum–Production, Technology, Chemistry, and Quality, Part IV" *CRC Critical Reviews in Food Science and Nutrition* 25–3:185–282.
Govindarajan (1991) "Capsicum–Production, Technology, Chemistry, and Quality, Part V" *CRC Critical Reviews in Food Science and Nutrition* 29–6:435–474.
Rouhi (1996) "Chili Pepper Studies Paying Off With Hot Birdseed And Better Analgesics" *C & EN* pp. 30–31.
Fuller (1990) "The Human Pharmacology of Capsaicin" *Arch. Int. Pharmacadyn.* 303:157–166.
Levenson (1995) "Accounting for Taste" *The Science Jan., Feb.*:15–16.

Primary Examiner—Michael G. Wityshyn
Assistant Examiner—Janet M. Kerr
Attorney, Agent, or Firm—Morgan & Finnegan, L.L.P.

[57] ABSTRACT

This invention relates to analgesic compositions obtained from the fruit of the Capsicum genus, in particular *Capsicum annuum* and more particularly to purees or extracts of sweet peppers. This invention further relates to therapeutic uses of such analgesic compositions.

12 Claims, No Drawings

ANALGESIC COMPOSITIONS FROM SWEET PEPPERS AND METHODS OF USE THEREOF

FIELD OF THE INVENTION

This invention relates to analgesic compositions obtained from the fruit of the Capsicum family, in particular *Capsicum annuum* and more particularly this invention relates to purees or extracts of sweet peppers. This invention further relates to therapeutic uses of such analgesic compositions.

BACKGROUND

A primary focus of drug research is the development of analgesics to be used in pain management.

New analgesics are often herbs derived from or plants.

For example, capsaicin, a vanillyl alkaloid which is the pungent component of hot peppers, is an analgesic. (Cordell and Araujo (1993) *The Annals of Pharmacotherapy* 27:330; Levinson (1995) *The Sciences* January/February: 13–15)). Therapeutically capsaicin has been used successfully to treat several painful conditions including rheumatoid arthritis, osteoarthritis, and various peripheral neuropathic disorders. (Cordell and Aravo (1993)). However, the usefulness of capsaicin as a therapeutic is limited by its adverse effects including burning and erythema. Moreover, these side effects can persist over time.

Given the comprehensive therapeutic applications of analgesics, there is an enormous medical and health requirement for analgesics with limited side effects.

SUMMARY OF THE INVENTION

It is an object of this invention to provide an analgesic composition obtained from the fruit of the genus Capsicum.

It is a further object of this invention to provide analgesic compositions from a natural source that is safe and effective.

It is yet another object of this invention to provide methods of producing the analgesic compositions described herein as well as methods of use thereof.

This and other objects of the invention have been obtained by providing analgesic compositions obtained from the fruit of the genus Capsicum and methods of producing the same. In particular, analgesic compositions have been obtained from the fruit of the genus *Capsicum annuum*, in particular sweet peppers. These analgesic compositions may be produced in a variety of ways, such as by pureeing of sweet peppers and either concentrating or extracting the puree. This invention further relates to methods of use thereof.

DETAILED DESCRIPTION OF THE INVENTION

This invention relates to analgesic compositions obtained from the fruit of the variety *Capsicum annuum* and methods of producing analgesic using the compositions disclosed herein. Specifically this invention relates to purees, extracts or concentrates of sweet peppers and therapeutic uses thereof as an analgesic composition. The analgesic compositions provided herein are based on an observation by the inventor that puree of sweet peppers exhibits an analgesic effect without the burning sensation that accompanies the use of capsaicin. This invention further relates to therapeutic uses thereof.

The analgesic compositions described herein may be produced in a variety of ways. In one embodiment sweet peppers are sliced and pureed by hand or mechanical means. The stems and seeds of the peppers may be removed prior to preparation of the puree. By way of example, sweet green bell peppers may be used to make the puree. The puree may be concentrated by conventional methodology, including, but not limited to, vacuum filtration. The puree may be used directly, concentrated, or diluted with an appropriate diluent, such as water.

Alternatively, an extract of sweet peppers or puree thereof may be prepared by conventional methodology. In one embodiment, an alcohol extraction may be performed by conventional methodology. By way of example, the sweet peppers or puree thereof may be extracted with short chain alcohols. Examples of short chain alcohols include, but are not limited to, methanol, ethanol and 2-propanol. In a preferred embodiment, methanol is used to extract the active ingredient from green bell peppers.

The formulations of the present invention comprise a puree, extract, or a concentrate thereof of sweet peppers as described above, optionally together with one or more pharmaceutically acceptable carriers and, and also optionally other therapeutic ingredients. Preferably, the puree, extract or concentrate thereof is obtained by from sweet peppers. The carrier(s) must be compatible with other ingredients of the formulation and not deleterious to the recipient thereof. The formulations may be conveniently prepared in unit dosage form and may be prepared by any method well-known in the pharmaceutical art.

All methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous intramuscular, subcutaneous, intralpleural, intraarticular or intrathecal, intraperitoneal administration conveniently comprise sterile aqueous solutions of the active ingredient with solutions which are preferably isotonic. Such formulations may be conveniently prepared by dissolving the active ingredient in water containing physiologically compatible substances such as isotonic sodium chloride, glycine, and the like, and having a buffered pH compatible with physiological conditions to produce an aqueous solution, and rendering the solution sterile. These may be present in unit or multi-dose containers, for example, sealed ampoules or vials.

The formulations of the present invention may incorporate a stabilizer. Illustrative stabilizers are polyethylene glycol, proteins, saccharides, amino acids, inorganic acids, and organic acids which may be used either independently or as admixtures. Two or more stabilizers may be used. These stabilizers may be used in aqueous solutions at the appropriate concentration and pH.

Additional pharmaceutical methods may be employed to control the duration of action. Controlled release preparations may be achieved by using polymers to complex or absorb the present active ingredient. The controlled delivery may be exercised by selecting appropriate macromolecules (for example polyester, polyamino acids, polyvinylpyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the present active material into particles of a polymeric material such as polyesters, polyamino acids, hydrogels, poly(lactic acid) or ethylene vinylacetate copolymers. Alternatively, instead of incorporating these materials into polymeric particles, it is possible to entrap these materials in microcapsules prepared, for example, by coacervation techniques or by interfacial polymerization, for example, hydroxymethylcellulose or gelatin-microcapsules and polymethylmethacrylate microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc magnesium stearate, crystalline cellulose, methyl cellulose, carboxymethyl cellulose, glycerin, sodium alginate or gum arabic among others.

Other modes of administration include, but are not limited to, topical: such as, ophthalamic, oral, nasal, vaginal, rectal, dermatological; and inhalation. The preparation of such ingredients is well known to those in the art. Therefore, the skilled artisan would be able to select the proper formulation ingredients.

The analgesic compositions of this invention may be pharmacologically and therapeutically useful where analgesics have been used in the prior art, including, but not limited to, the management of acute pain, chronic pain, neuralgias, other neurogenic pain syndromes, and post-operative pain in a subject. The therapeutically useful dosage of the analgesic used in the given therapy or treatment will vary depending on the seriousness of the condition, the time the individual has been afflicted with the condition, the weight of the individual, efficacy of the present active material and other parameters known to one skilled in the art. Based on such parameters the treating artisan will determine the therapeutically effective amount of the composition to be used for a given individual. Such therapies may be administered as often as necessary and for the period of time judged necessary by the artisan administering the treatment.

The present invention also provides a method of treating subjects afflicted with a condition amenable to analgesic treatment which comprises the step of administering to the subject a therapeutically effective amount of the sweet pepper puree, extract, or concentrates thereof, optionally with a pharmaceutically acceptable composition as described above. Administration of the analgesic composition may be for either a prophylactic or therapeutic use. When provided prophylactically, the composition is provided in advance of any symptom which might arise in the absence of analgesic treatment. When provided therapeutically, the composition is provided at (or shortly after) the onset of any symptoms. The therapeutic administration of the present composition serves to attenuate the painful condition. Examples of conditions that can be treated by this method include, but are not limited to, post operative, conjunctival, nasal, otic, rectal and vaginal pain.

The therapeutically effective amount of the sweet pepper puree, extract, or concentrate thereof to be used in the aforementioned treatments will vary depending on the seriousness of the pain. One of skill in the art will know the parameters to evaluate the response of the subject to the present compositions and establish the dosage based on those parameters.

All books articles or patents referenced herein are incorporated by reference. The following examples illustrate various aspects of the invention but are in no way intended to limit the scope thereof.

EXAMPLE 1

Analgesic Effect of Pepper Puree Materials

"Sweet" green, bell peppers (*Capsicum annuum grossum*) were obtained from the grocery section of a local supermarket. The stems, seeds and veins were removed and discarded, and the skin was cut into small, ½ in., squares. The pieces, 476 g, were pureed in a blender to a green mush. The puree was vacuum filtered (slowly) to give 260 mL of green aqueous suspension. The green suspension was again suction filtered giving 260 mL of green suspension filtrate topped with some foam.

The filtrate was apportioned as follows:
Preparation Designation & Description
A: 70 milliliter (mL) of filtrate
B: 35 mL of filtrate plus 35 mL of water
C: 7 mL of filtrate plus 63 mL of water The filter residue, solid green puree, was mixed with 200 mL of water, stirred and refiltered, to give 155 mL of pale green suspension. This suspension was apportioned as follows
Preparation Designation & Description
D: 70 mL of resuspension
E: 35 mL of resuspension plus 35 mL of water Rat Tail Flick Trails The rat tail flick list is a classic animal model designed to detect and evaluate agents which elevate the threshold for perception of pain. In this model, a pharmacologically altered pain threshold would result in a delay of rat tail flick to avoid a noxious stimulus, such as a heat lamp.

In this Example, the rats' tails were dipped briefly (1–3 sec) in the liquid; were allowed to air dry, then subjected to a heat lamp. Time was measured to the first tail flick response.
Preparation Designation and Description (3 rats per trial)
A: baseline 2.54 sec. Trial (avg) 8.60 sec
C: baseline 2.37 sec. Trial (avg) 6.52 sec
D: baseline 2.83 sec. Trial (avg) 5.43 sec The tails of animals used to determine baseline were dipped in water and air dried prior to exposure to the heat lamp. As shown by the trials, puree of green bell pepper induced an analgesic effect as evidenced by a significantly prolonged time to tail flick.

EXAMPLE 2

Materials

Sweet Red peppers Sweet red peppers were obtained, cut and pureed as before. 258 g of red peppers gave 157 mL of a red-orange opaque filtrate.
Preparation Designation & Description
F: 70 mL of red pepper filtrate
Yellow Bell Peppers Sweet yellow bell peppers were obtained, cut and pureed as above. 246 g of peppers gave 150 mL of yellow opaque filtrate.
Preparation Designation & Description
G: 70 mL of yellow pepper filtrate
Alcohol Extracts of Green Bell Peppers Stems, veins and seeds were removed from 4 green peppers as before, and 436 g of small pieces of pepper were pureed. Suction filtration of the puree gave 275 mL of green suspension. This mixture was concentrated under reduced pressure (water pump, rotary evaporator) at 500C for 3 hr. A mixture of green solid and solution resulted: weight 12.5 g.

The mixture of solid and solution was mixed with 100 mL of methanol, stoppered, and kept at room temperature for 65 hr, then gravity filtered, resulting in a clear green solution. This solution was concentrated under reduced pressure, affording 8.00 g of green foam.

The residue from concentration of the methanol extract was covered with 70 mL of water. Swirling the mixture for 10 minutes (min.) produced an opaque green solution. All of the extract residue dissolved.

Preparation Designation & Description
H: 70 mL of MeOH residue dissolved in water.
I: 10% dilution of H in water
J: 1% dilution of H in water
K: 0.1% dilution of H in water

TABLE I

| Preparation Description | n* | Tail-Flick Test 0 minutes** | 30 minutes*** |
|---|---|---|---|
| Baseline+ (NO WATER IMMERSION) | 20.0 | 2.76 (0.11) | |
| Water Immersion | 5 | 4.76 (0.39) | 2.64 (0.09) |
| A: Green Pepper Filtrate (10.0%) | 6 | 7.21 (0.81) | 2.78 (0.25) |
| B: Green Pepper Filtrate (50%) | 6 | 6.44 (0.60) | 3.12 (0.34) |
| C: Green Pepper Filtrate (10%) | 6 | 6.10 (0.41) | 3.07 (0.33) |
| D: Green Pepper residue extract (100%) with $H_2O$ | 6 | 5.98 (0.38) | 2.97 (0.38) |
| E: Green Pepper residue extract (50%) with $H_2O$ | 6 | 5.69 (0.38) | 3.12 (0.40) |
| F: Red Pepper Filtrate (100%) | 6 | 5.64 (0.45) | 3.05 (0.34) |
| G: Yellow Pepper Filtrate (100%) | 6 | 4.91 (0.19) | 2.77 (0.20) |
| H: Green Pepper Methanol (100%) | 9 | 8.49 (0.45) | 3.87 (0.24) |
| I: Green Pepper Methanol (10%) | 6 | 7.13 (0.46) | 3.05 (0.35) |
| J: Green Pepper Methanol (1%) | 6 | 6.03 (0.42) | 3.25 (0.34) |
| K: Green Pepper Methanol (0.1%) | 8 | 5.30 (0.13) | 3.06 (0.18) | n* = number of animals.
The numbers in parenthesis represent the standard error of the mean.
**1st test after drying of applied preparation
***reapplication of noxious stimuli
+Baseline, animals received no treatment As shown in Table I, there is an enhanced analgesic effect with green and red peppers. The greatest analgesic effect was found in the filtrate of the green pepper puree at 100% concentration, and the resuspended aqueous solution of the methanol extract of the green pepper puree at 100% and 10% concentrations. The resuspended aqueous solution of the methanol extract of the green pepper puree at 100% concentration exhibited the most prolonged duration of action.

The present invention has been described in some detail by way of illustrations and examples for the purpose of clarity of understanding. It will be obvious that certain changes and modifications may be practiced within the scope of the appended claims.

What is claimed is:

1. A method for providing analgesia to a subject, comprising administering to the subject a composition comprising an amount of a filtrate of red, yellow or green sweet bell pepper puree, or an extract or concentrate of said filtrate, effective to provide analgesia without producing a burning sensation.

2. The method of claim 1 wherein the extract is an alcohol extract.

3. The method according to claim 1 in which the composition is administered nasally, topically, systemically, intramuscularly, subcutaneously, intraperitoneally, intrapleurally, intraarticularly, intrathecally, rectally, vaginally, or by inhalation.

4. The method of claim 1, wherein the composition comprises a filtrate of the sweet pepper puree optionally admixed with a pharmaceutical carrier.

5. The method of claim 1, wherein the composition comprises a concentrate of the filtrate of the sweet pepper puree optionally admixed with a pharmaceutical carrier.

6. The method of claim 1, wherein the composition comprises an extract of the filtrate of the sweet pepper puree optionally admixed with a pharmaceutical carrier.

7. The method of claim 6, wherein the extract is an alcohol extract.

8. The method of claim 7, wherein the alcohol is a short chain alcohol.

9. The method of claim 8, wherein the alcohol is methanol.

10. The method of claim 1, wherein the sweet bell pepper puree is a green bell pepper puree.

11. The method of claim 10, wherein the composition comprises a filtrate of green bell pepper puree.

12. The method of claim 1, wherein the composition is formulated as a controlled-release formulation.

* * * * *